US00PP37417P2

(12) United States Plant Patent
Serrador

(10) Patent No.: US PP37,417 P2
(45) Date of Patent: May 12, 2026

(54) STRAWBERRY PLANT VARIETY NAMED 'MC18-20 Cleopatra'

(50) Latin Name: ***Fragaria* x *ananassa Duchesne* x *Rozier***
Varietal Denomination: MC18-20 Cleopatra

(71) Applicant: MASIÁ CISCAR S.A., Lepe (ES)

(72) Inventor: Enrique Masiá Serrador, Lepe (ES)

( * ) Notice: Subject to any disclaimer, the term of this patent is extended or adjusted under 35 U.S.C. 154(b) by 0 days.

(21) Appl. No.: 19/050,087

(22) Filed: Feb. 10, 2025

(51) Int. Cl.
*A01H 5/08* (2018.01)
*A01H 6/74* (2018.01)

(52) U.S. Cl.
USPC ..... Plt./208
CPC ..... *A01H 6/7409* (2018.05); *A01H 5/08* (2013.01)

(58) Field of Classification Search
USPC ..... Plt./208
CPC ..... A01H 6/7409; A01H 5/08
See application file for complete search history.

*Primary Examiner* — Keith O. Robinson
(74) *Attorney, Agent, or Firm* — Furr Law Firm; Jeffrey M. Furr

(57) ABSTRACT

A new and distinct variety of strawberry plant named 'MC18-20 Cleopatra', particularly selected for its early beginning of flowering; and early time of beginning of fruit ripening, is disclosed.

10 Drawing Sheets

Latin name: Botanical classification: *Fragaria x ananassa Duchesne x Rozier.*

Varietal denomination: The varietal denomination of the claimed variety of strawberry plant is 'MC18-20 Cleopatra'.

BACKGROUND OF THE INVENTION

Cultivated strawberry is a hybrid species of the genus *Fragaria* that is grown worldwide for its fruit. Modern strawberry was first bred in Brittany, France, in the 18" century by crossing *Fragaria virginiana* with *Fragaria chiloensis*. Strawberry fruit is an aggregate accessory fruit, with the fleshy part of the fruit being derived from the receptacle that holds the ovanes.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa* Duchesne x Rozier), which has been denominated as 'MC18-20 Cleopatra'.

'MC18-20 Cleopatra' was subsequently asexually propagated via runners, and underwent further testing at test plots in Spain. The present variety has been found to be stable.

The variety 'MC18-20 Cleopatra' is a variety that was produced from a cross made in the winter of 2018. It is unknown which is the female parent and which is the male parent. The clones (daughter plants) of 'MC18-20 Cleopatra' were initially propagated from a single mother plant in 2018. Since then, 'MC18-20 Cleopatra' has been preserved through annual cycles of asexual propagation using stolons at a facility in Lepe, Huelva (Spain).

'MC18-20 Cleopatra' exhibits the following distinguishing characteristics when grown under normal horticultural practices in Spain:

1. Fruit: difference in shape of terminal and other fruits;
2. Many stolons;
3. The early beginning of flowering; and
3. The early time of beginning of fruit ripening.

'MC18-20 Cleopatra' was particularly selected for the shelf-life and flavor of its fruit, high mid- to late season yield when grown in Spain.

DESCRIPTION OF THE DRAWINGS

This new strawberry plant is illustrated by the accompanying photographs which show fruit of the plant, flowers, leaves, and the plants. The colors shown are as true as can be reasonably obtained by conventional photographic procedures. The average age of the plants in the Figures are 3.5 months.

DETAILED BOTANICAL DESCRIPTION

Figure 1:
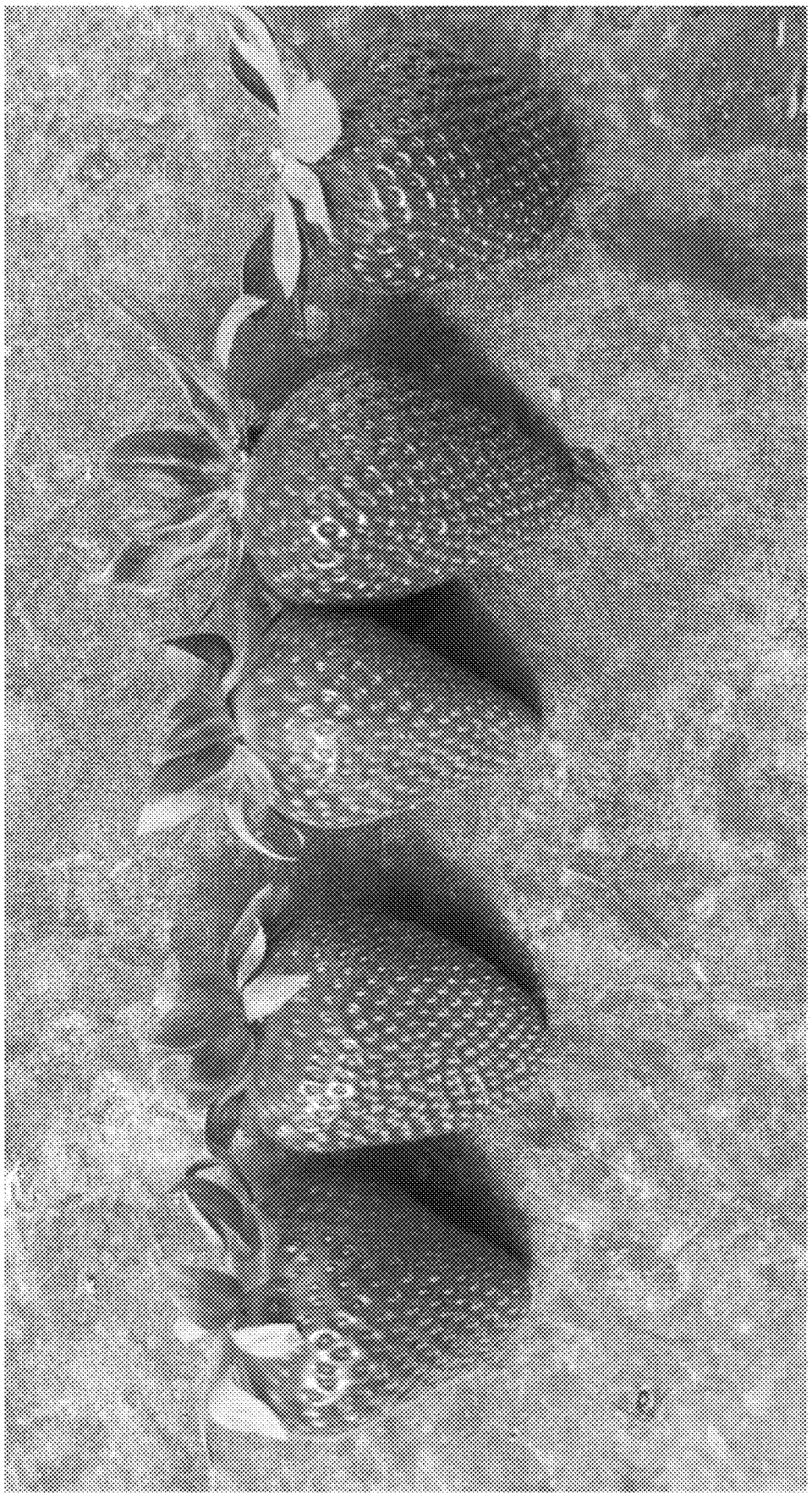
FIG. 1 illustrates whole fruit of variety 'MC18-20 Cleopatra'.
Figure 2:
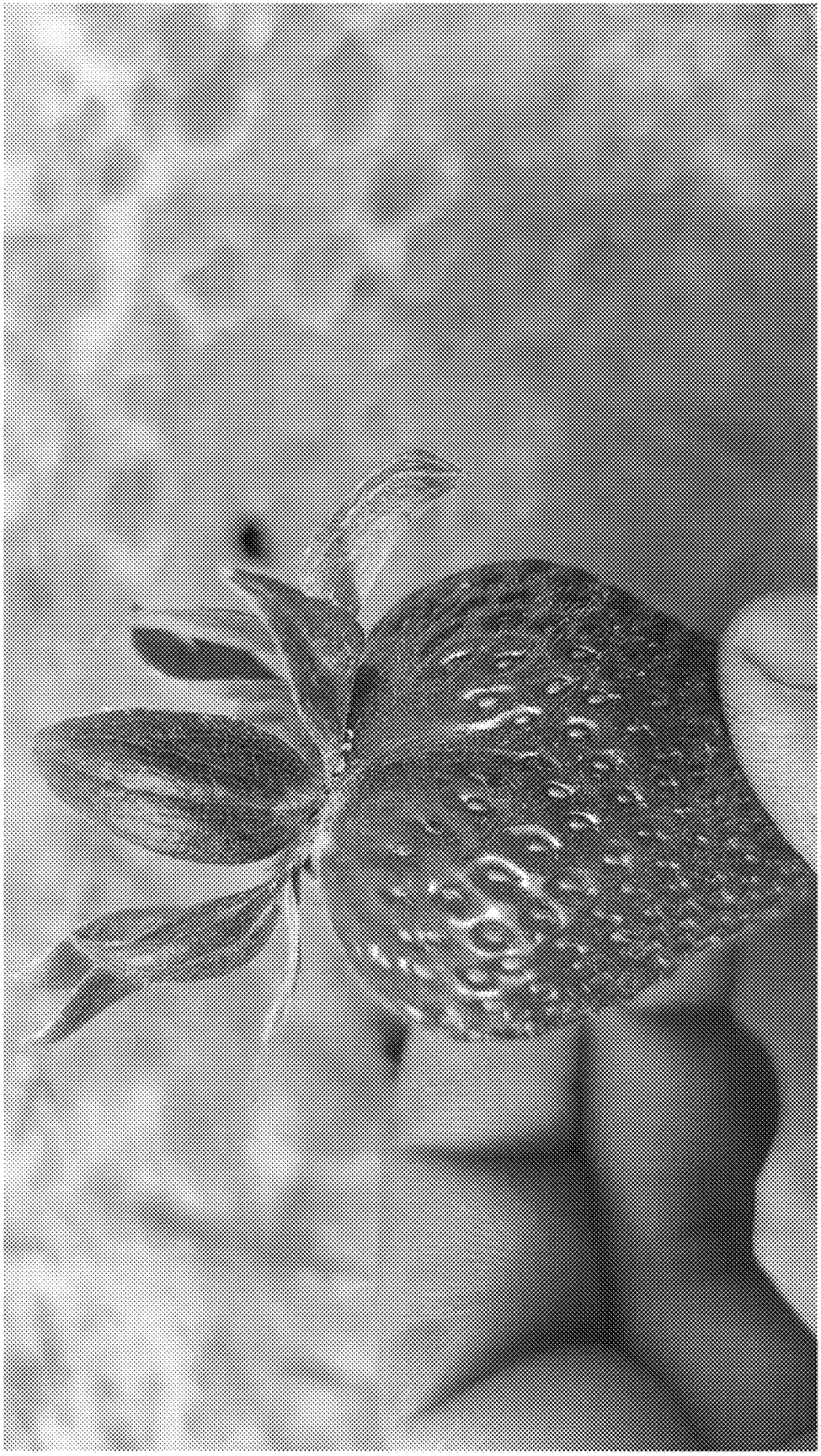
FIG. 2 illustrates the whole fruit of variety 'MC18-20 Cleopatra' being held.
Figure 3:
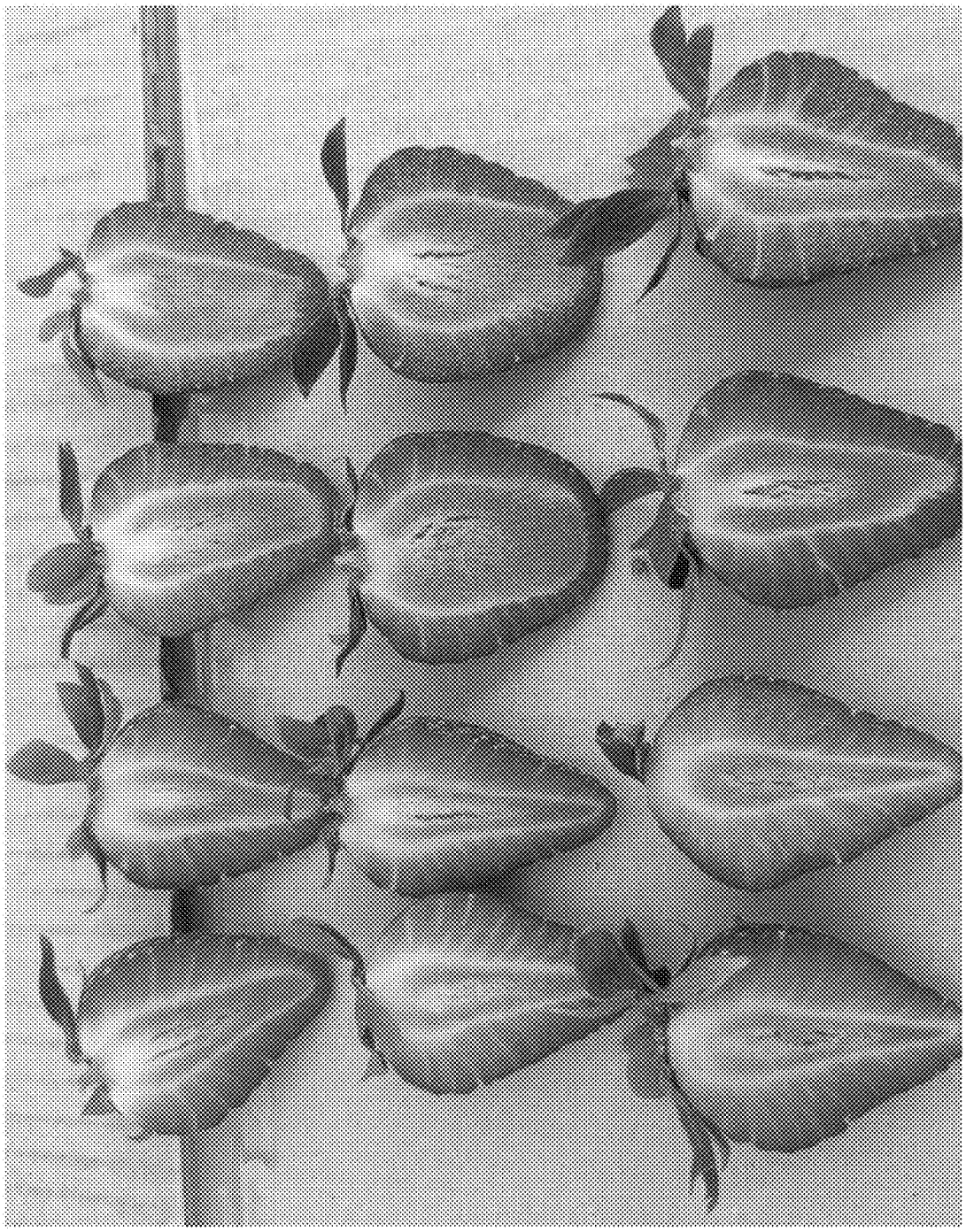
FIG. 3 illustrates longitudinal sections of fruit of variety 'MC18-20 Cleopatra'.
Figure 4:
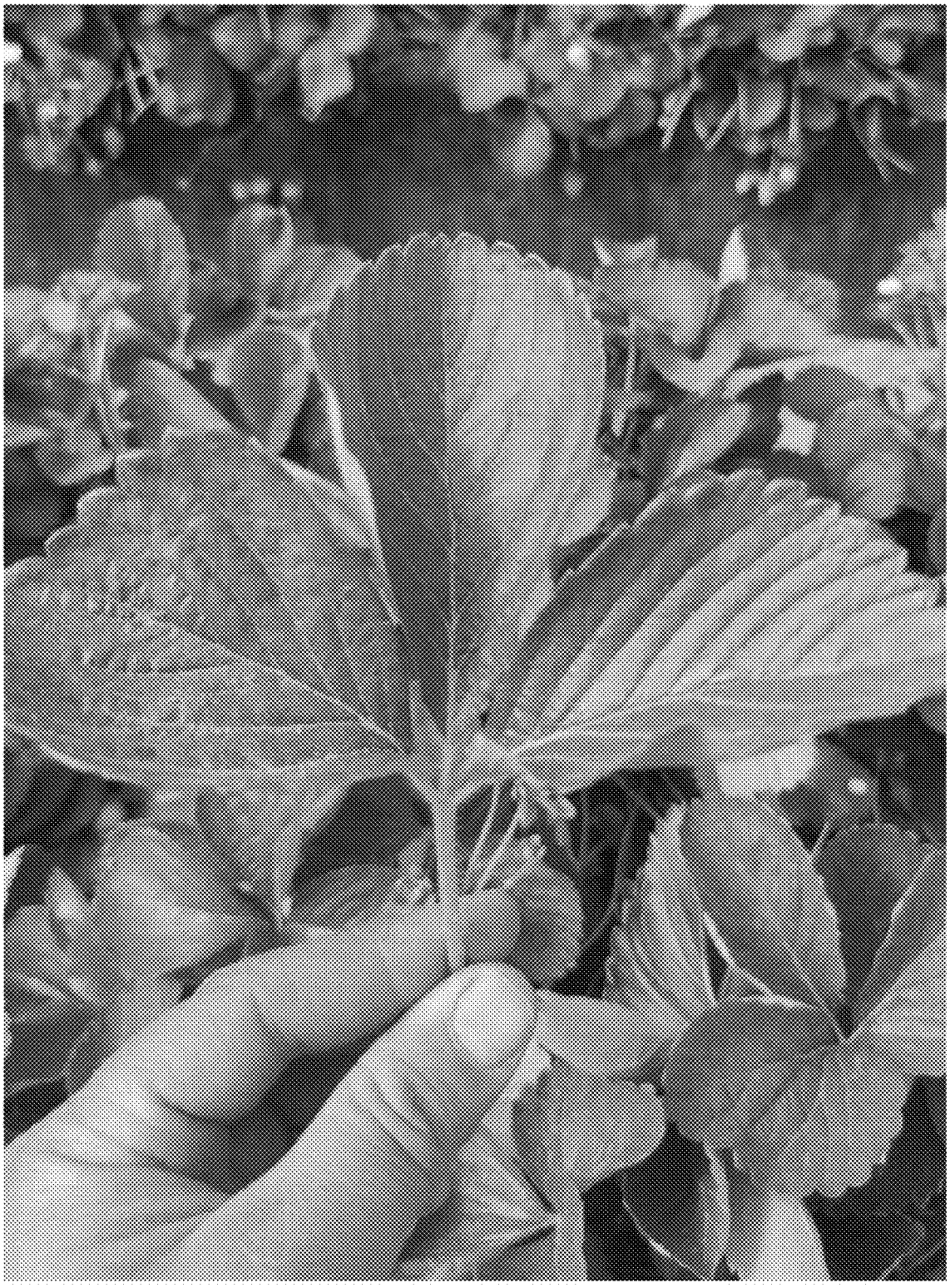
FIG. 4 illustrates leaves of variety 'MC18-20 Cleopatra'.
Figure 5:
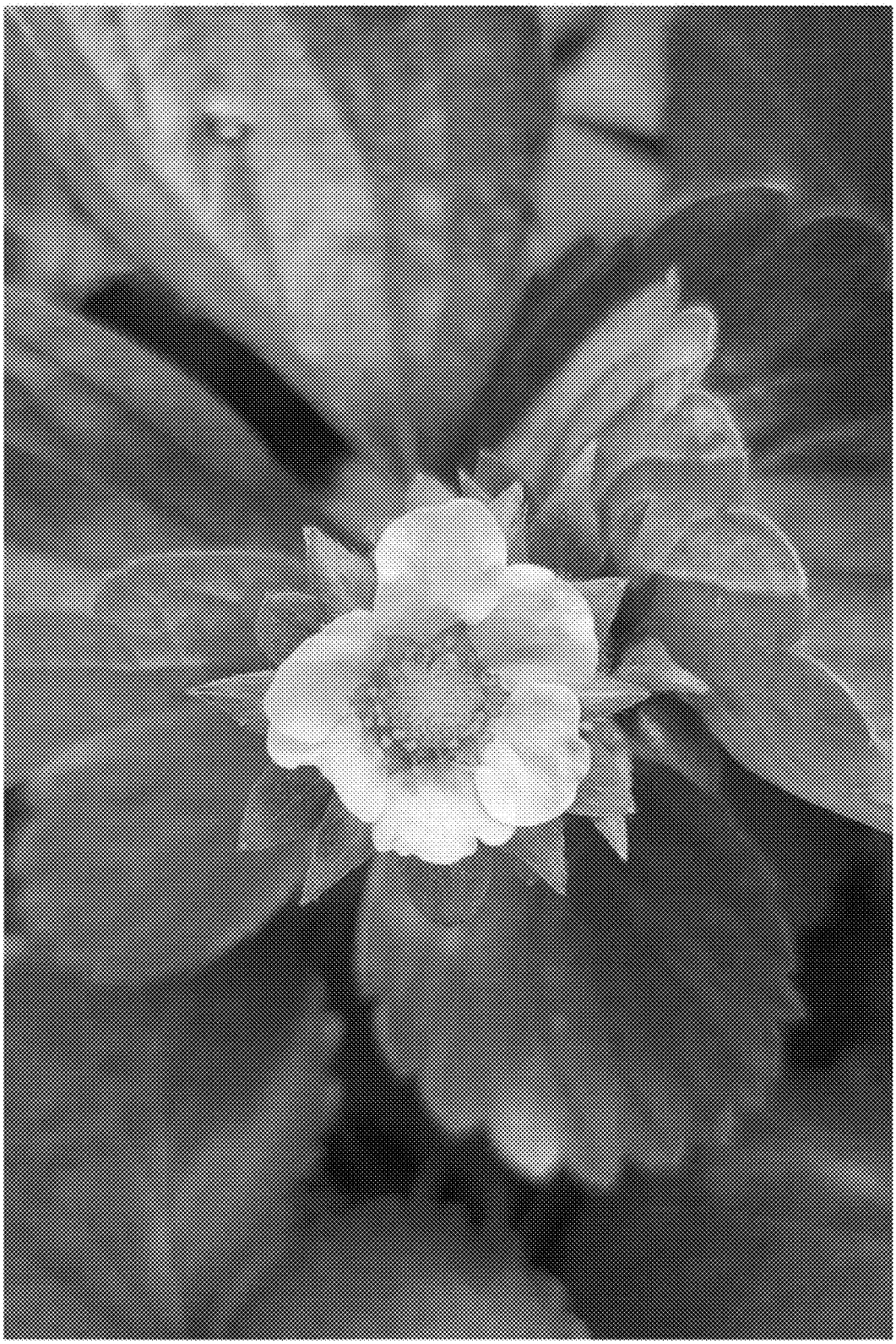
FIG. 5 illustrates the upper surfaces of flowers of variety 'MC18-20 Cleopatra'.
Figure 6:
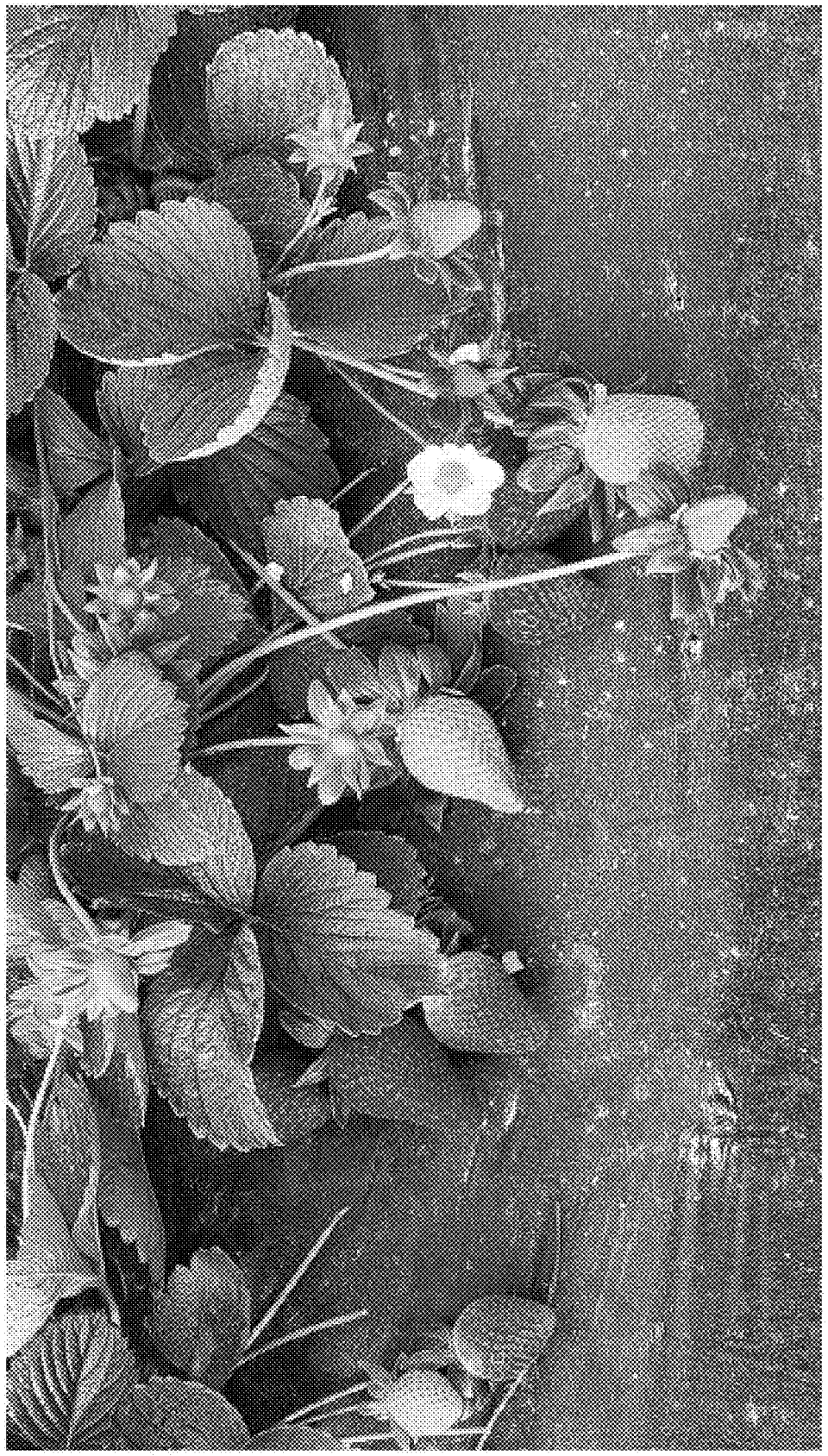
FIG. 6 illustrates a view of whole plants of variety 'MC18-20 Cleopatra'.
Figure 7:
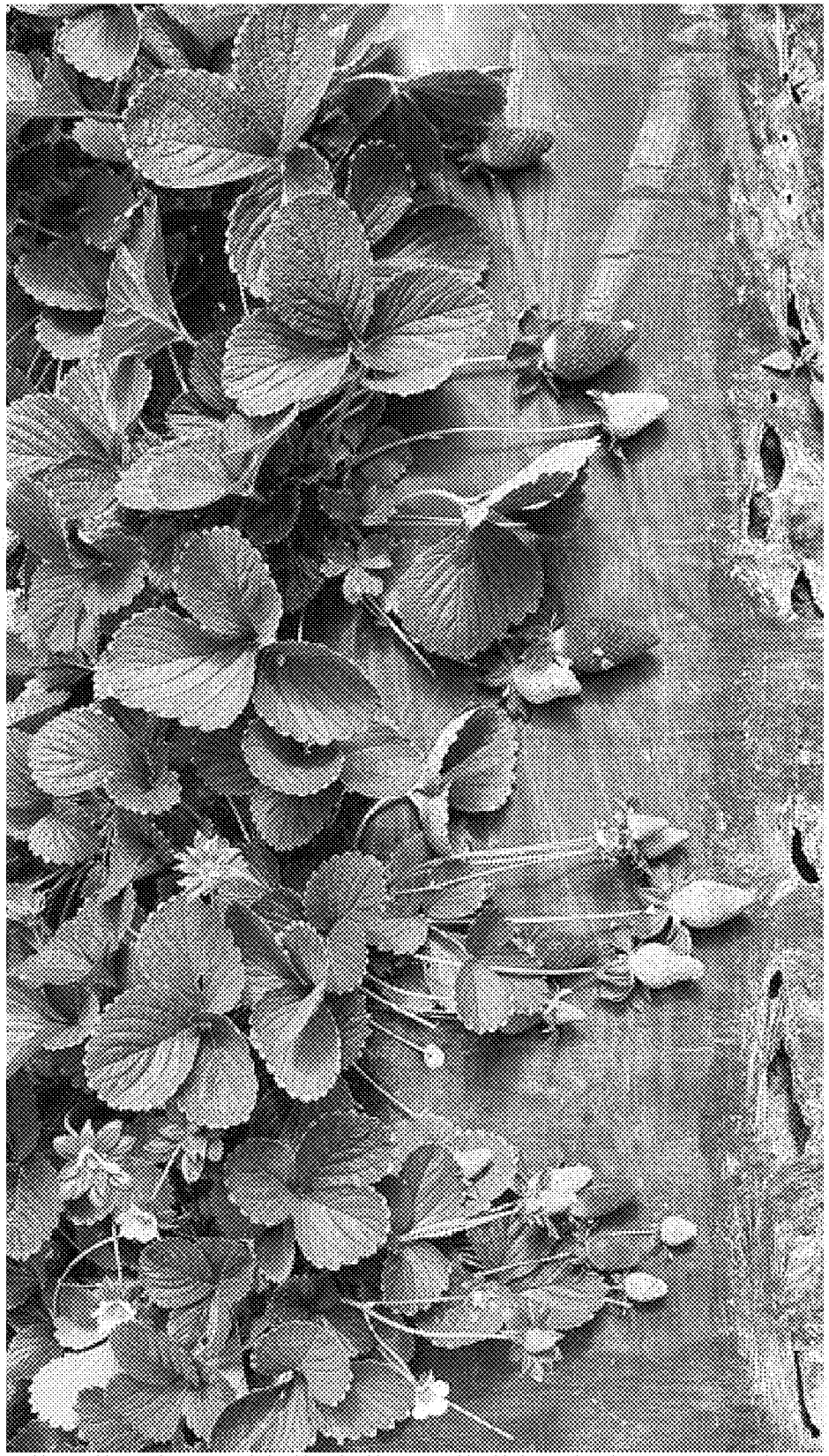
FIG. 7 illustrates an additional view of whole plants of variety 'MC18-20 Cleopatra'.
Figure 8:
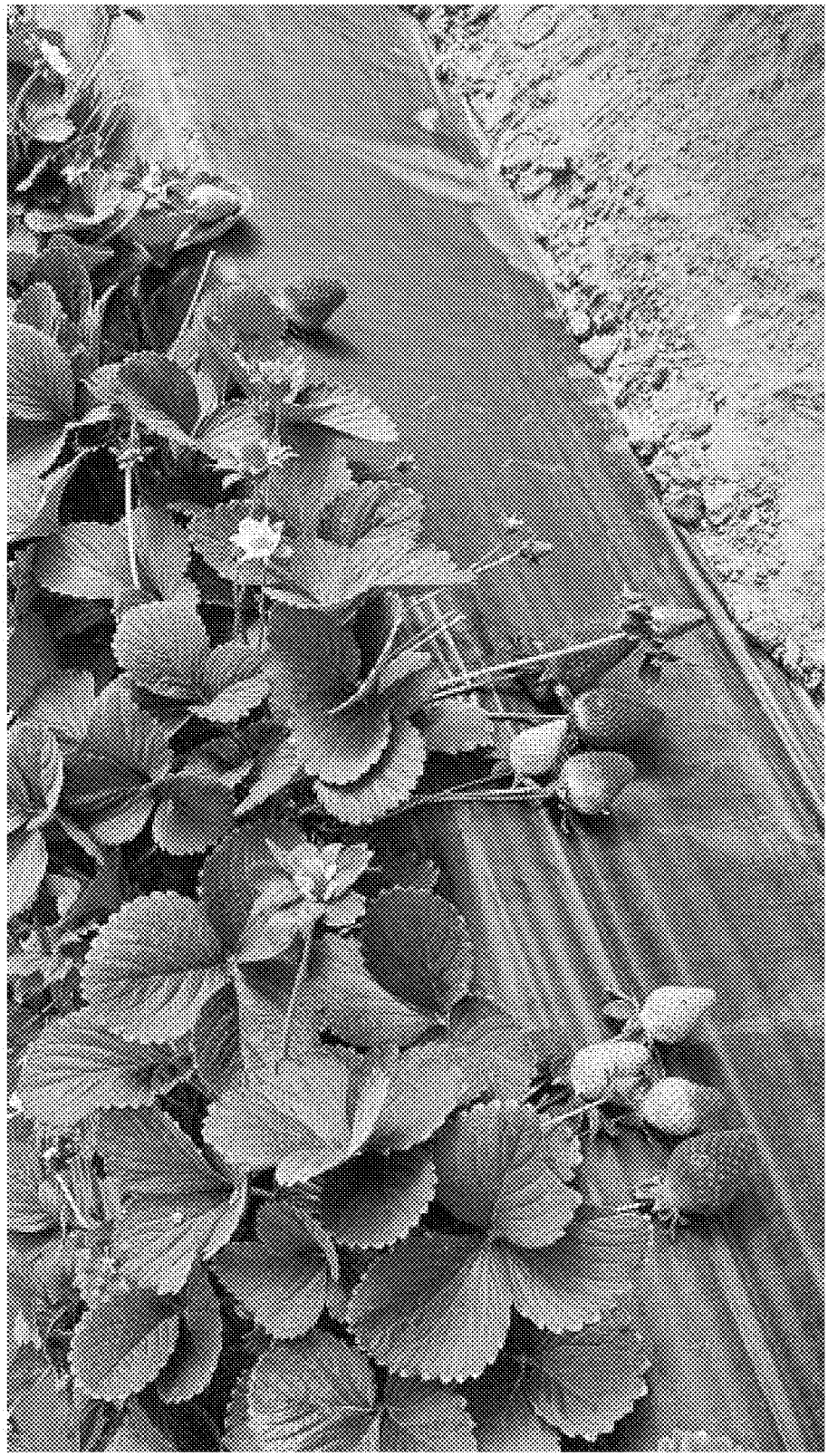
FIG. 8 illustrates another additional view of whole plants of variety 'MC18-20 Cleopatra'.
Figure 9:
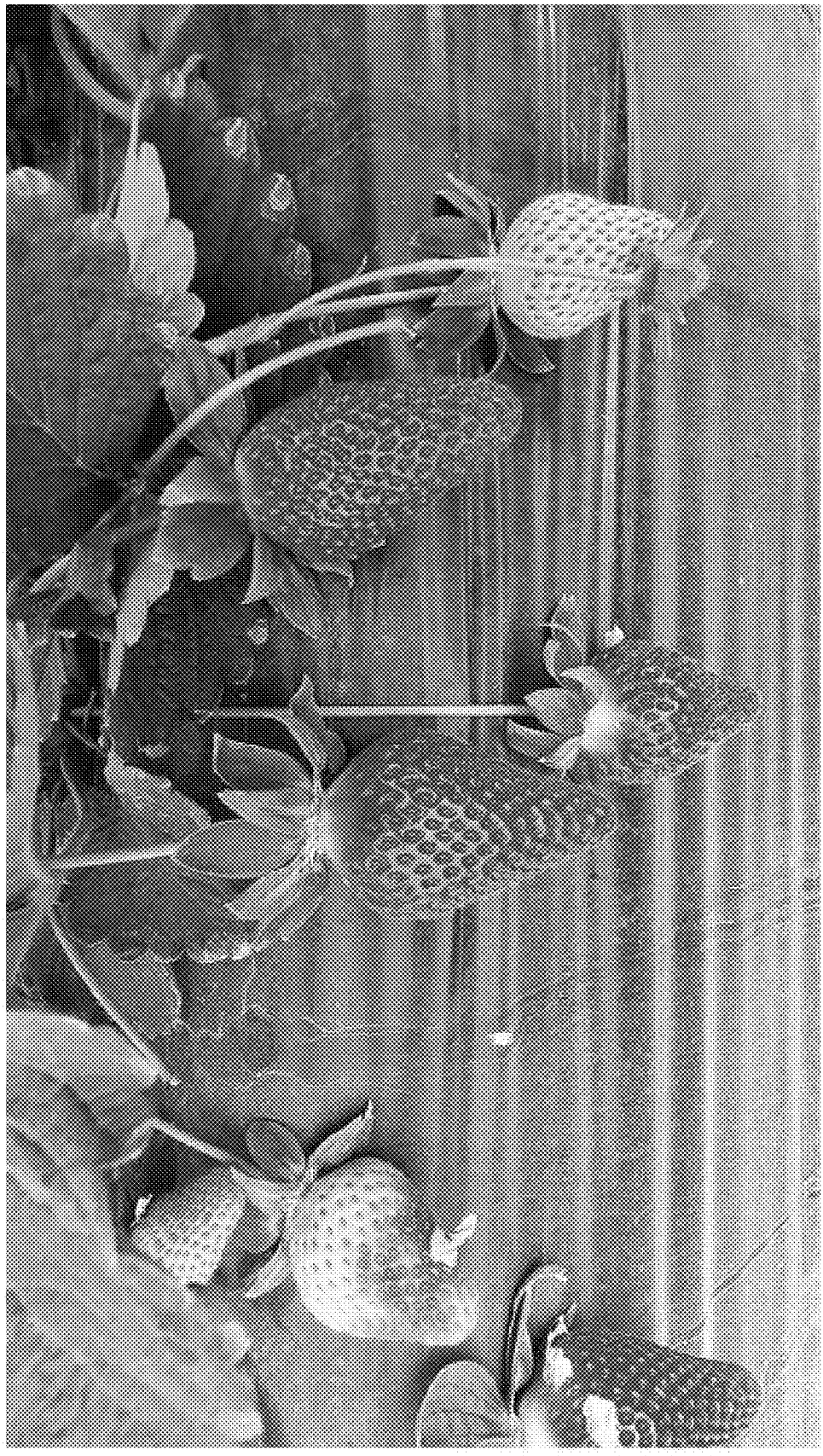
FIG. 9 illustrates another additional view of whole plants of variety 'MC18-20 Cleopatra'.
Figure 10:
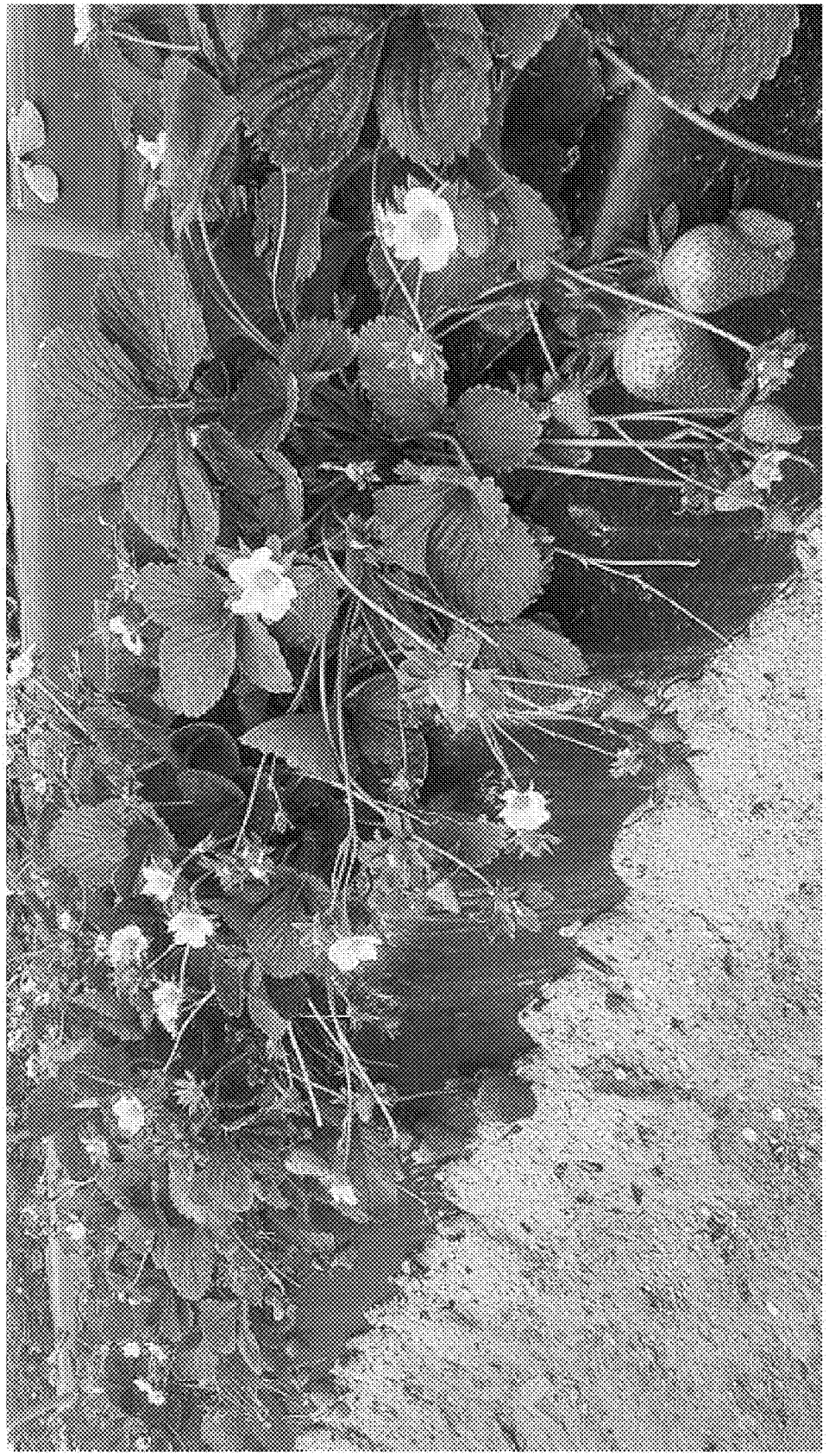
FIG. 10 illustrates another additional view of whole plants of variety 'MC18-20 Cleopatra'.

The following detailed descriptions set forth the distinctive characteristics of 'MC18-20 Cleopatra'. The data which define these characteristics is based on observations taken in Spain. This description is in accordance with UPOV terminology. Color designations, color descriptions, and other phenotypical descriptions may deviate from the stated values and descriptions depending upon variation in environmental, seasonal, climatic, and cultural conditions. 'MC18-20 Cleopatra' has not been observed under all possible environmental conditions.

The variety 'MC18-20 Cleopatra' Cleopatra is a variety that was produced from a cross made in the winter of 2018. It is unknown which is the female parent and which is the male parent. The clones (daughter plants) of 'MC18-20 Cleopatra' were initially propagated from a single mother plant in 2018. Since then, 'MC18-20 Cleopatra' has been preserved through annual cycles of asexual propagation using stolons at a facility in Lepe, Huelva (Spain).

The indicated values represent averages calculated from measurements of several plants. Color references are primarily to The R.H.S. Colour Chart of The Royal Horticultural Society of London (R.H.S.) (2015 edition). Descriptive terminology follows the Plant Identification Terminology, An Illustrated Glossary, 2" edition by James G. Harris and Melinda Woolf Harris, unless where otherwise defined.

Classification:

*Species.*—*Fragaria* x *ananassa* Duchesne x Rozier.

*Common name.*—Strawberry.

*Denomination.*—'MC18-20 Cleopatra'.

Breeding scheme: Crossing.

Parents: Unknown.

Plant:

*Growth habit.*—Upright.

*Runners.*—Flowering.

Stolon:

*Average number of daughter plants per square foot.*—Many, the multiplication index is between 40 and 50 after 6 months of nursery cultivation, and from there it can reach a multiplication rate of 80 or 100.

*Position of the inflorescence in relation to the foliage of the plant.*—ABOVE.

Leaf:

*Number of leaflets.*—Three only.

*Color of upper surface.*—RHS 139A (Dark yellowish green).

*Variegation.*—Absent.

*Size.*—Medium.

*Shape of base.*—Obtuse.

*Margin.*—Serrate to crenate.

*Shape in cross section.*—Convex.

*Rugosity.*—Very weak.

*Average leaf length.*—12.9 cm.

*Average leaf width.*—10.6 cm.

*Glossiness of the leaf.*—MEDIUM.

Petiole:

*Attitude of hairs.*—Horizontal.

Pedicel:

*Attitude of hairs.*—Slightly outwards.

Flower:

*Flower diameter* (*petal tip to petal tip on non-flattened flower*).—Medium.

*Size of calyx in relation of corolla.*—Larger.

*Stamen.*—Present.

*Color of upper side.*—RHS 1 (white).

*Flower diameter.*—5 cm.

*Sepals.*—5.2 cm.

*Petals.*—3.1 cm.

*Arrangement of the petals of the flower.*—OVERLAPPING.

N) *Flower diameter.*—5.

Fruit:

*Length in relation to width.*—Moderately longer.

*Size.*—Medium to large.

*Shape.*—Conical; wedged.

*Color.*—Medium red RHS 35 (medium red).

*Position of achenes.*—Below surface.

*Position of calyx attachment.*—Raised.

*Fruit diameter of calyx in relation to diameter to fruit.*—Slightly larger.

*Attitude of sepals.*—Outwards.

*Average length of fruit.*—4.1 cm.

*Average width of fruit.*—6.8 cm.

Production:

*Flowering interval.*—Early.

*Harvest interval.*—Very early to early.

*Type of bearing.*—Not remontant.

COMPARISON WITH COMMERCIAL VARIETIES

| Denomination (s) of variety(ies) similar to the candidate variety | Characteric(s) in which your candidate variety differs from the similar variety(ies) | Describe the expression of the characteristic(s) for the similar variety(ies) | Describe the expression of the characteristic(s) for your candidate variety |
|---|---|---|---|
| 'A13 29' | Fruit: difference in shape of terminal and other fruits | Moderate | None or very slight |
| 'A13 29' | Plant: number of stolons | Medium | Many |
| 'A13 299' | Time of beginning of fruit ripening | Medium | Very early to early |

A13-29, the plant variety A13-29 is protected under U.S. Plant Pat. No. 32,078, application Ser. No. 15/932,974 before USPTO.

I claim:

1. A new and distinct variety of strawberry plant named 'MC18-20 Cleopatra' as shown and described herein.

* * * * *